US009132069B2

(12) United States Patent
Hecht et al.

(10) Patent No.: US 9,132,069 B2
(45) Date of Patent: Sep. 15, 2015

(54) ONE COMPONENT SELF-ADHESIVE DENTAL COMPOSITION, PROCESS OF PRODUCTION AND USE THEREOF

(71) Applicant: 3M INNOVATIVE PROPERTIES COMPANY, Saint Paul, MN (US)

(72) Inventors: Reinhold Hecht, Kaufering (DE); Andrea Stippschild, Landsberg (DE); Vitore Hasanaj, Weilheim (DE); Gioacchino Raia, Türkenfeld (DE); Manfred Ludsteck, Geretsried (DE); Rainer Guggenberger, Herrsching (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/360,373

(22) PCT Filed: Nov. 30, 2012

(86) PCT No.: PCT/US2012/067159
§ 371 (c)(1),
(2) Date: May 23, 2014

(87) PCT Pub. No.: WO2013/082337
PCT Pub. Date: Jun. 6, 2013

(65) Prior Publication Data
US 2014/0329205 A1 Nov. 6, 2014

(30) Foreign Application Priority Data
Dec. 1, 2011 (EP) .................................. 11191541

(51) Int. Cl.
*A61K 6/083* (2006.01)
*C09J 133/10* (2006.01)
*C09J 133/14* (2006.01)
*C09J 175/16* (2006.01)
*A61C 13/15* (2006.01)

(52) U.S. Cl.
CPC .............. *A61K 6/083* (2013.01); *A61C 19/003* (2013.01); *C09J 133/10* (2013.01); *C09J 133/14* (2013.01); *C09J 175/16* (2013.01)

(58) Field of Classification Search
CPC ... A61K 6/083; C09J 133/062; C08L 33/062; C08L 43/02
USPC ........................................ 523/118; 433/228.1
See application file for complete search history.

(56) References Cited

U.S. PATENT DOCUMENTS

| 3,729,313 A | 4/1973 | Smith |
|---|---|---|
| 3,741,769 A | 6/1973 | Smith |
| 3,808,006 A | 4/1974 | Smith |
| 4,071,424 A | 1/1978 | Dart |
| 4,250,053 A | 2/1981 | Smith |
| 4,259,075 A | 3/1981 | Yamauchi |
| 4,394,403 A | 7/1983 | Smith |
| 4,499,251 A | 2/1985 | Omura |
| 4,537,940 A | 8/1985 | Omura |
| 4,539,382 A | 9/1985 | Omura |
| 4,642,126 A | 2/1987 | Zador |
| 4,652,274 A | 3/1987 | Boettcher |
| 4,737,593 A | 4/1988 | Ellrich |
| 4,795,823 A | 1/1989 | Schmitt |
| 4,872,936 A | 10/1989 | Engelbrecht |
| 5,130,347 A | 7/1992 | Mitra |
| 5,530,038 A | 6/1996 | Yamamoto |
| 5,545,676 A | 8/1996 | Palazzotto |
| 5,624,260 A | 4/1997 | Wilcox |
| 5,865,803 A | 2/1999 | Major |
| 5,893,714 A | 4/1999 | Arnold |
| 6,444,725 B1 | 9/2002 | Trom |
| 6,458,868 B1 | 10/2002 | Okada |
| 6,572,693 B1 | 6/2003 | Wu |
| 6,899,948 B2 | 5/2005 | Zhang |
| 7,214,726 B2 * | 5/2007 | Qian ............................ 523/116 |
| 2004/0097613 A1 | 5/2004 | Hecht |
| 2004/0110864 A1 | 6/2004 | Hecht |
| 2007/0054978 A1 * | 3/2007 | Futigami et al. ............. 523/116 |
| 2007/0172789 A1 | 7/2007 | Muller |
| 2012/0115106 A1 * | 5/2012 | Qian et al. ................. 433/203.1 |

FOREIGN PATENT DOCUMENTS

| EP | 0712622 | 5/1996 |
|---|---|---|
| EP | 1051961 | 11/2000 |
| EP | 1340472 | 9/2003 |
| EP | 2153811 | 2/2010 |
| GB | 1316129 | 5/1973 |
| JP | 2011-121869 | 6/2011 |
| WO | WO 95-22956 | 8/1995 |
| WO | WO 2009-151957 | 12/2009 |

OTHER PUBLICATIONS

1507 Extended EP Search Report for EP11191541.9, PCT/US2012/067159, Date May 8, 2012, 5 pgs.
International Search Report for PCT International Application No. PCT/US2012/067159 mailed on Apr. 5, 2013, 4pgs.

* cited by examiner

Primary Examiner — Tae H Yoon

(57) ABSTRACT

The invention relates to a one-component self-adhesive composition for dental use comprising radically polymerizable component(s) with an acidic moiety as component A, radically polymerizable component(s) without an acidic moiety as component (B), an oxidizing agent comprising persulfate(s) as component (C), transition metal component(s) as component (D), photoinitiator system(s) as component (E), optionally non acid-reactive filler(s) as component (F), and optionally additive(s) as component (G).

17 Claims, No Drawings

ONE COMPONENT SELF-ADHESIVE DENTAL COMPOSITION, PROCESS OF PRODUCTION AND USE THEREOF

CROSS REFERENCE TO RELATED APPLICATIONS

This application is a national stage filing under 35 U.S.C. 371 of PCT/US2012/067159, filed Nov. 30, 2012, which claims priority to European Application No. 11191541.9, filed Dec. 1, 2011, the disclosures of which are incorporated by reference in their entirety herein.

FIELD OF THE INVENTION

The invention relates to a one-component self-adhesive dental composition comprising a photoinitiator system, an oxidizing agent and a copper compound. The composition can be used for various dental applications.

BACKGROUND ART

Dental composites are well known in dentistry and are widely used as restorative materials (filling composites) or as cements (resin cements) in the prosthodontic field. Generally composites are hydrophobic in nature and contain as main parts of the formulation inorganic fillers, a (meth)acrylate based resin matrix and initiators for the radical polymerization.

To get adhesion to enamel and dentin, composites typically require a pre-treatment of the tooth surface by using a bonding agent or a bonding system. This may result in a rather complex and time consuming procedure. Therefore attempts were made to develop self-adhesive composites which avoid the use of an additional bonding agent/system resulting in materials which are easier and faster to use for the dentist.

In the prosthodontic area self-adhesive resin cements are well established materials in the meantime. A commercially available product is e.g. RelyX™ Unicem (3M ESPE). These materials are formulated as two-component systems.

Two-component systems are not always easy to apply and use. Thus, it is generally desirable to have a one-component system.

In the restorative area also a self-adhesive, light-curable, one-component composite material recently appeared on the market (Vertise™ Flow, Kerr Company).

EP 2 153 811 A2 (Kerr) relates to a single-part, light-curable, self-adhering dental restorative composition comprising three different polymerizable monomers, a photoinitiator and one or more fillers.

US 2004/0110864 (Hecht et al.) describes self-adhesive compositions. If the composition is cured by photopolymerization it is possible to formulate one-component systems. If the composition comprises a redox initiator system comprising e.g. an organic peroxide and activator then for reasons of storage stability peroxide and activator are present in spatially separated parts.

In a particular example a composition is described with an initiator system, which can comprise sodium toluene sulfinate, sodium peroxodisulfate, a barbituric acid derivative and copper acetate.

JP 2011-121869 relates to a chemical polymerization catalyst composition for dental curable materials comprising an aryl borate compound, acidic compound, inorganic peroxide and bivalent copper compound. The system is formulated as a two-component system.

SUMMARY

It would be desirable to have a one-component, preferably light-curable composition showing good adhesion not only to enamel but also dentin surfaces combined with good mechanical and esthetic properties.

In one embodiment the present invention features a one-component self-adhesive composition for dental use comprising
a) radically polymerizable component(s) with acid functionality,
b) radically polymerizable component(s) without acid functionality,
c) an oxidizing agent comprising persulfate(s)
d) transition metal component(s)
e) photoinitiator system,
f) optionally non acid-reactive filler(s), and
g) optionally additives.

A further embodiment of the invention is directed to a process of producing the composition as described in any of the preceding claims comprising the steps of mixing and/or kneading.

Other embodiments, features and advantages of the present invention will be apparent from the following detailed description, drawings, and claims.

Unless defined differently, for this description the following terms shall have the given meaning:

A composition can be classified as "storage stable", if it remains stable over a considerable long period of time (at least about 4 weeks to more than about 12 months under ambient conditions). A storage stable composition does typically not show decomposition of the components contained therein or premature polymerization over time. Moreover, the features intended to be achieved by the composition shall not diminish more than desired.

"One component" means that all of the components mentioned are present in the composition during storage and use. That is, the composition to be applied or used is not prepared by mixing different parts of the composition before use. In contrast to one-component compositions, those compositions are often referred to as two-component compositions (e.g. being formulated as powder/liquid, liquid/liquid or paste/paste compositions).

A "dental composition" or a "composition for dental use" or a "composition to be used in the dental field" is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

A "hardenable component or material" or "polymerizable component" is any component which can be cured or solidified e.g. by heating to cause polymerization, chemical crosslinking, radiation-induced polymerization or crosslinking by using a redox initiator. A hardenable component may contain only one, two, three or more polymerizable groups. Typical examples of polymerizable groups include unsaturated carbon groups, such as a vinyl group being present i.a. in a (methyl)acrylate group.

An "ethylenically unsaturated acidic compound" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3H$ or sulfinic acid residues such as —$SO_2H$.

A "filler" contains all fillers being present in the hardenable composition. Only one type of filler or a mixture of different fillers can be used.

A "non-surface treated filler" is a filler having a surface which has not been exposed to reactive substances resulting in a modification of the surface of the filler to make the filler more compatible or reactive with other components of the composition.

As used herein "adhesive" or "dental adhesive" refers to a composition used as a pre-treatment on a dental structure (e.g., a tooth) to adhere a "dental material" (e.g., "restorative" an orthodontic appliance (e.g., bracket), or an "orthodontic adhesive") to a dental surface. An "orthodontic adhesive" refers to a composition used to adhere an orthodontic appliance to a dental (e.g., tooth) surface. Generally, the dental surface is pre-treated, e.g., by etching, priming, and/or applying an adhesive to enhance the adhesion of the "orthodontic adhesive" to the dental surface.

As used herein, a "dental surface" or "tooth surface" refers to the surface of tooth structures (e.g., enamel, dentin, and cementum) and bone.

As used herein, a "self-etching" composition refers to a composition which bonds to a dental surface without pre-treating the dental surface with an etchant. Preferably, a self-etching composition can also function as a self-primer wherein no separate etchant or primer is used.

As used herein, a "self-adhesive" composition refers to a composition that is capable of bonding to a dental surface without pre-treating the dental surface with a primer or bonding agent. Preferably, a self-adhesive composition is also a self-etching composition wherein no separate etchant is used.

As used herein, an "untreated" dental surface refers to a tooth or bone surface that has not been treated with an etchant, primer, or bonding agent prior to application of a self-etching adhesive or a self-adhesive composition.

As used herein, an "unetched" dental surface refers to a tooth or bone surface that has not been treated with an etchant prior to application of a self-etching adhesive or a self-adhesive composition of the present invention.

As used herein, an "etchant" refers to an acidic composition that is capable of fully or partially solubilizing (i.e., etching) a dental surface. The etching effect can be visible to the naked human eye and/or instrumentally detectably (e.g., by light microscopy). Typically, an etchant is applied to the dental structure surface for a period of about 10 to 30 seconds.

As used herein, "(meth)acryl" is a shorthand term referring to "acryl" and/or "methacryl". For example, a "(meth)acryloxy" group is a shorthand term referring to either an acryloxy group (i.e., $CH_2{=}CH{-}C(O){-}O{-}$) and/or a methacryloxy group (i.e., $CH_2{=}C(CH_3){-}C(O){-}O{-}$).

A "nano-sized filler" is a filler, the individual particles thereof have a size in the region of nanometers, e.g. an average particle diameter of less than about 200 nm. Useful examples are given in U.S. Pat. No. 6,899,948 and U.S. Pat. No. 6,572,693, the content of which especially with regard to nano-sized silica particles is herein incorporated by reference.

An "initiator or initiator system" is a substance being able to start the curing process of a hardenable compound.

A "curing, hardening or setting reaction" is used interchangeable and refers to a reaction wherein physical properties such as viscosity and hardness of a composition changes over the time due to a chemical reaction between the individual components.

A "derivative" is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

The term "visible light" is used to refer to light having a wavelength of about 400 to about 800 nanometers (nm).

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

The inventive composition is suitable to solve at least one of the above mentioned objectives e.g. providing a one-component, self-adhesive dental composition with good adhesive properties especially with respect to dentin surfaces.

Surprisingly it was found that compounding a photo-initiator-system together with an oxidizing agent selected from or comprising persulfate(s) and a transition metal component(s) results in a sufficiently stable composition, that is, in a composition which does not cure during a reasonable storage period unless exposed to radiation.

Besides sufficient storage stability, the composition is self-adhesive. That is, the composition adheres to dental surfaces without a pre-treatment using e.g. an etchant and/or a bonding system.

Providing the composition as a one-component dental formulation facilitates the application by the practitioner during use. The composition can be applied as it is, using common equipment already present in the dental office.

The composition shows good adhesion performance both to enamel and dentin without the use of a bonding agent or a bonding system.

Besides the feature of self-adhesiveness the composition typically has overall good mechanical and aesthetic properties.

The inventive composition can typically be characterized by at least one of the following features after hardening:
Flexural strength determined according to ISO 4049:2000 at least about 50 MPa or at least about 70 or at least about 90 MPa,
E-Modulus determined according to ISO 4049:2000 at least about 3500 MPa or at least about 4500 or at least about 5500 MPa.
adhesion to dentin determined according to wire loop adhesion (see experimental part): at least about 5 MPa or at least about 7 or at least about 9 MPa,
adhesion to enamel determined according to wire loop adhesion (see experimental part): at least about 7 MPa or at least about 9 or at least about 11 MPa, Depending on the intended use, the viscosity of the composition is typically adjusted.

If the composition is used as dental fissure sealant or dental flowable, suitable viscosities include e.g. from about 1 to about 150 Pa*s or from about 10 to about 120 Pa*s (23° C.; shear rate: 100 1/s).

If desired, the viscosity can be determined as follows: The viscosity can be measured using a Physica MCR 301 Rheometer (Anton Paar, Graz, Austria) with a cone/plate geometry CP25-1 under controlled shear rate at 23° C. The diameter is 25 mm, the cone angle 1°, and the separation between the cone tip and the plate 49 µm. The shear rate is ramped down logarithmically from $1000\ s^{-1}$ to $1\ s^{-1}$, with a total of 23 data points being collected. The integration time for each data point was 10 s.

The invention provides a composition which can be hardened in an acceptable time frame, e.g., less than about 300 seconds (s) or less than about 180 s or less than about 120 s, and to a sufficient depth using visible light source equipment already available in the dental office or electronics fabrication facilities.

The inventive composition, if dissolved or dispersed in water (e.g. 1 g in 10 ml) typically shows a pH value in the range from about 0 to about 5 or from about 1 to about 4. That is, the composition as a whole is acidic.

The inventive composition comprises one or more radically polymerizable components with acid moiety as component (A) or part of component (A).

If desired, a mixture of different radically polymerizable components with acid moiety can be used.

The radically polymerizable components with acid moiety can typically be characterized by at least one of the following features:

Molecular weight (Mw): from about 70 to about 700 g/mol or from about 100 to about 600 or from about 200 to about 500 g/mol,
Viscosity: from about 0.1 to about 10 Pa*s, or from about 0.2 to about 5 Pa*s or from about 0.5 to about 2 Pa*s measured at 23° C., and/or
Refractive index: from about 1.42 to about 1.55 (nD).

Using a component (A) with at least one of the following features can be preferred, especially, if the hardenable composition should show sufficient adhesiveness:
polymerizable moiety comprising a (meth)acrylate group,
acidic moiety comprising a phosphor, carbon or sulphur containing group,
molecular weight being in the range from about 70 to about 700 or from about 100 to about 600 or from about 200 to about 500 g/mol.

The ethylenically unsaturated acidic compound can typically be represented by formula (I)

$$A_n\text{-}B\text{—}C_m \quad (I)$$

with A being an ethylenically unsaturated group, such as a (meth)acryl moiety,
B being a spacer group, such as (i) linear or branched C1 to C12 alkyl, optionally substituted with other functional groups (e.g. halogenides, OH or mixtures thereof) (ii) C6 to C12 aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and
C being an acidic group, with m, n=1, 2, 3, 4, 5 or 6,
wherein the acidic group comprises one or more carboxylic acid residues, such as —COOH or —CO—O—CO—, phosphoric acid residues, such as —O—P(O)(OH)OH, phosphonic acid residues, such as C—P(O)(OH)(OH), sulphonic acid residues, such as —SO₃H or sulfinic acid residues such as —SO₂H.

Specific examples of ethylenically unsaturated acidic compounds as component (A) include, but are not limited to glycerol phosphate mono(meth)acrylate, glycerol phosphate di(meth)acrylate, hydroxyethyl(meth)acrylate (e.g., HEMA) phosphate, bis((meth)acryloxyethyl)phosphate, (meth)acryloxypropyl phosphate, bis((meth)acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis((meth)acryloxyoctyl)phosphate, (meth)acryloxydecyl phosphate, bis((meth)acryloxydecyl) phosphate, caprolactone methacrylate phosphate, citric acid di- or tri-methacrylate, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like. Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid moiety include, for example, polymerizable bisphosphonic acids; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, e.g., in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.).

The unsaturated acidic compound can be present in the composition in an amount of at least about 3 or at least about 5 or at least about 10 wt.-%, wt.-% with respect to the weight of the whole composition.

However, amounts of up to about 80 or up to about 70 or up to about 60 wt.-% can still be useful, wt.-% with respect to the weight of the whole composition.

Useful amounts include from about 3 to about 80 or from about 5 to about 70 or from about 10 to about 60 wt.-% with respect to the weight of the whole composition.

The inventive composition comprises one or more radically polymerizable component(s) without acid moiety as component (B) or as part of component (B).

This component is typically a free-radically polymerizable material, including ethylenically unsaturated monomer, monomers or oligomers or polymers.

Component (B) may also comprise a hydroxyl group, a 1,3-diketo moiety or both.

Such polymerizable materials include mono-, di- or polyacrylates and methacrylates such as methyl acrylate, methyl methacrylate, ethyl(meth)acrylate, isopropyl(meth)acrylate, n-hexyl(meth)acrylate, stearyl(meth)acrylate, allyl(meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-acryloxy)]-p-ethoxy-phenyldimethylmethane, bis[1-(3-acryloxy-2-hydroxy)]p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

Further polymerizable components are di(meth)acrylates of ethoxylated bis-phenol A, for example 2,2'-bis(4-(meth)acryloxytetraethoxyphenyl)propanes, urethane(meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8(9)-tricyclo[$5.2.1.0^{2,6}$]decylmethyl triglycolate. Suitable are also 2,2-bis-4-(3-methacryloxy-2-hydroxypropoxy)phenylpropane (Bis-GMA), 2,2-bis-4-(3-methacryloxypropoxy)phenyl propane, 7,7,9-trimethyl-4,13-dioxo-3,14-dioxa-5,12-diazahexadecane-1,16-dioxy dimethacrylate (UDMA), urethane (meth)acrylates and di(meth)acrylates of bishydroxymethyl-tricyclo-($5.2.1.0^{2,6}$)decane.

These ethylenically unsaturated monomers can be employed in the dental composition(s) either alone or in combination with the other ethylenically unsaturated monomers.

In addition or besides those components, other hardenable components which can be added include oligomeric or polymeric compounds, such as polyester urethane(meth)acrylates, polyether urethane(meth)acrylates, polycarbonate urethane(meth)acrylates and poly(meth)acrylate urethane(meth) acrylates. The molecular weight of these compounds is typically less than 20,000 g/mol, particularly less than 15,000 g/mol and in particular less than 10,000 g/mol.

Adding one or more polymerizable components with a hydroxyl group and/or a 1,3-diketo moiety as component (B) or part of component (B) can sometime be preferred.

Adding these components may facilitate the production process.

It was also found that using this kind of polymerizable component(s) may also result in an increased adhesion of the composition especially to dentin surfaces.

Specific examples include: polymerizable monomers, oligomers or polymers containing a hydroxide group and a polymerizable unsaturated group such as an acryloyl group, a methacryloyl group, a vinyl group or an allyl group and the like. Monomers are particularly preferable. These compounds include 2-hydroxyethyl(meth)acrylate (HEMA), 2- or 3-hydroxypropyl(meth)acrylate, 4-hydroxybutyl(meth)acrylate, 5-hydroxypentyl(meth)acrylate, 6-hydroxyhexyl(meth)acrylate, 10-hydroxydecyl(meth)acrylate, dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl(meth)acrylate, 2-hydroxypropyl-1,3-di(meth)acrylate, 3-hydroxypropyl-1,2-di(meth)acrylate, N-(meth)acryloyl-1,2-dihydroxypropylamine, N-(meth)acryloyl-1,3-dihydroxypropylamine, adducts of phenol and glycidyl(meth)acrylate, for example, 1-phenoxy-2-hydroxypropyl(meth)acrylate, 1-naphthoxy-2-hydroxypropyl(meth)acrylate, bisphenol A diglycidyl(meth)acrylate and the like, 2-hydroxyethyl(meth)acrylate, 2-hydroxypropyl(meth)acrylate and 2,3-dihydroxypropyl(meth) acrylate are particularly preferable.

An example of a polymerizable component with 1,3-diketo group is acetoacetoxy ethylmethacrylate (AAEMA).

If desired, mixtures of one or more of these components can be used. The individual components might be named as component (B1), (B2), (B3), etc.

In a specific embodiment component (B) comprises mixtures of unsaturated hydroxyl- and/or 1,3-diketo functional compounds (e.g. HEMA and/or AA-EMA) with unsaturated compounds not having these functionalities. Component (B) is typically present in the composition in an amount of at least about 5 wt.-% or at least about 10 wt.-% or at least about 20 wt.-% with respect to the weight of the whole composition.

If present, the amount of component (B) contained in the composition is typically up to about 65 wt.-% or up to about 55 wt.-% or up to about 45 wt.-% with respect to the weight of the whole composition.

Typical ranges include from about 5 to about 65 or from about 10 to about 55 or from about 20 to about 45 or wt.-% with respect to the weight of the whole composition.

The composition comprises an oxidizing agent as component (C) or part of component (C). The oxidizing agent is selected from persulfate(s) or mixtures thereof.

The oxidizing agent should be sufficiently stable in order to be compounded into a dental composition. The oxidizing agent does typically not contain organic residues, e.g. carbon-carbon moieties and such can be characterized as an inorganic substance.

According to one embodiment, the persulfate or its radicals which may be produced during the hardening reaction is water-soluble.

Water-soluble means that the persulfate can be dissolved in water, e.g. by dissociating into ions.

Persulfates which can be used can be characterized by the following formula:

$$D_2S_2O_8 \quad (II)$$

with D being selected from Li, Na, K, $NH_4$, $NR_4$, with R being selected from H and $CH_3$.

Examples of persulfate(s) which can be used include, $Na_2S_2O_8$, $K_2S_2O_8$, $(NH_4)_2S_2O_8$ and mixtures thereof.

The amount of persulfate which can be used is not particularly limited. The persulfate should be used in an amount sufficient to achieve the intended purpose.

Useful amounts include:
at least about 0.1 wt.-% or at least about 0.3 wt.-% or at least about 0.5 wt.-% with respect to the whole composition and/or
up to about 10 wt.-% or up to about 5 wt.-% or up to about 2 wt.-% with respect to the whole composition.

Typical ranges include from about 0.1 wt.-% to about 10 wt.-% or from about from about 0.3 wt.-% to about 5 wt.-% or from about 0.5 wt.-% to about 2 wt.-% with respect to the whole composition.

If the amount of persulfate used is too high, mechanical and esthetic properties are reduced.

If the amount of persulfate used is too low, adhesion to tooth structure (i.e. enamel and dentin) is reduced.

If desired and in order to simplify the production process, the persulfate can be pre-mixed with filler particles and added to the remaining components of the composition during production.

The inventive composition comprises one or more transition metal component(s) as component (D) or part of component (D).

Suitable transition metal component(s) include organic and/or inorganic salt(s) from titanium, vanadium, chromium, manganese, iron, cobalt, nickel, copper and/or zinc.

Useful salts include acetate(s), chloride(s), sulphate(s), benzoate(s), acetylacetonate(s), naphthenate(s), carboxylate(s), bis(1-phenylpentan-1,3-dione) complexes, salicylate(s), complexes with ethylenediaminetetraacetic acid of either of the transition metals and mixtures thereof.

According to one embodiment, the transition metal component is in an oxidation stage, which allows the component to be reduced. Useful oxidation stages include +2, +3, +4, +5, +6 and +7, as applicable.

Copper component(s) are sometimes preferred. The oxidation stage of copper in the copper component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis (1-phenylpentan-1,3-dione) complex (copper procetonate), copper salicylate, complexes of copper with thiourea, ethylenediaminetetraacetic acid and/or mixtures thereof. The copper compounds can be used in hydrated form or free of water.

Especially preferred is copper acetate.

The amount of transition metal component which can be used is not particularly limited. The transition metal salt should be used in an amount sufficient to achieve the intended purpose.

The transition metal component is typically present in the composition in an amount of at least about 0.0001 wt.-% or at least about 0.001 wt.-% or at least about 0.01 wt.-%.

The amount of transition metal component contained in the composition is typically up to about 3 wt.-% or up to about 2 wt.-% or up to about 1.8 wt.-%.

Typical ranges include from about 0.0001 to about 3 or from about 0.001 to about 2 or from about 0.01 to about 1.8 wt.-%.

If the amount of transition metal component used is too high, esthetic properties might be reduced.

If the amount of transition metal component used is too low, adhesion to tooth structure (i.e. enamel and dentin) might be reduced.

The inventive composition comprises one or more photoinitiator systems as component (E) or part of component (E). As known to the skilled person, photoinitiator systems can include more than one component.

A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between about 400 and about 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat. No. 4,071,424 and WO 2009151957, which are herein incorporated by reference.

A typical example of such a system is the combination of camphorquinone and an amine. Using EDMAB (ethyl 4-dimethylamino benzoate) can be preferred.

Alternatively, the resin can be combined with a three components or ternary photoinitiator system such as described in U.S. Pat. No. 5,545,676 and WO 2009151957, which are incorporated herein by reference.

In the ternary photoinitator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. No. 3,729,313, U.S. Pat. No. 3,741,769, U.S. Pat. No. 3,808,006, U.S. Pat. No. 4,250,053 and U.S. Pat. No. 4,394,403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing SbF$_5$OH$^-$ or AsF$_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: ACO(X)$_b$B, where X is CO or CR$^5$R$^6$, where R$^5$ and R$^6$ can be the same or different, and can be hydrogen, alkyl, alkaryl or aralkyl, b is zero or one, and A and B different and can be substituted (having one or more non-interfering substituents) can be the same or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Alternatively, free-radical initiators useful in the invention include the class of acylphosphine oxides and bisacylphosphine oxides.

Suitable acylphosphine oxides can be described by the general formula

$(R^9)_2$-P(=O)—C(=O)—R$^{10}$ (III)

wherein each R$^9$ individually can be a hydrocarbyl group such as alkyl, cycloalkyl, aryl, and aralkyl, any of which can be substituted with a halo-, alkyl- or alkoxy-group, or the two R$^9$ groups can be joined to form a ring along with the phosphorous atom, and wherein R$^{10}$ is a hydrocarbyl group, an S-, O-, or N-containing five- or six-membered heterocyclic group, or a —Z—C(=O)—P(=O)—(R$^9$)$_2$ group, wherein Z represents a divalent hydrocarbyl group such as alkylene or phenylene having from 2 to 6 carbon atoms.

Preferred acylphosphine oxides are those in which the R$^9$ and R$^{10}$ groups are phenyl or lower alkyl- or lower alkoxy-substituted phenyl. By "lower alkyl" and "lower alkoxy" is meant such groups having from 1 to 4 carbon atoms. Examples can also be found e.g. in U.S. Pat. No. 4,737,593.

Suitable bisacylphosphine oxides can be described by the general formula

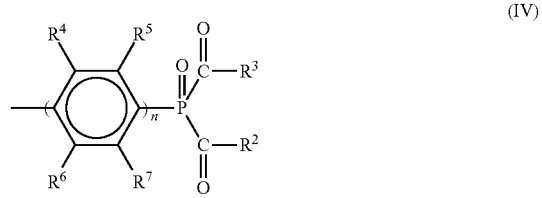

(IV)

wherein n is 1 or 2, and R$^4$, R$^5$, R$^6$ and R$^7$ are H, C1-4 alkyl, C1-4 alkoxyl, F, Cl or Br; R$^2$ and R$^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or R$^2$ and R$^3$ are joined to form a ring containing from 4 to 10 carbon atoms and being optionally substituted by 1 to 6 C1-4 alkyl radicals.

Further examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6- dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)-phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (IRGACURE™ 819, Ciba Specialty Chemicals, Tarrytown, N.Y.) is sometimes preferred.

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta$5-2,4-cyclopentadien-1-yl)-bis(2,6-difluoro-3-(1H-pyrrol-1-yl)phenyl)titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Useful amounts for photoinitiator system(s) include:
at least about 0.1 wt.-% or at least about 0.3 wt.-% or at least about 0.5 wt.-% and/or
up to about 5 wt.-% or up to about 4 wt.-% or up to about 3 wt.-%.

Typical ranges include from about 0.1 wt.-% to about 5 wt.-% or from about 0.3 wt.-% to about 4 wt.-% or from about 0.5 wt.-% to about 3 wt.-%.

The inventive composition may also comprise one or more non acid-reactive fillers as component (F) or part of component (F).

A non-acid reactive filler is a filler which does not undergo an acid/base reaction with an acid.

Examples of acid reactive fillers include certain fluoroalumina glasses (sometimes also referred to as GIZ glasses; those glasses typically have a weight ratio of Al2O3 to SiO2 of at least 1 to 2, hydroxides, oxides and carbonates of alkaline earth metals like $Ca(OH)_2$, $Mg(OH)_2$, CaO, MgO, $CaCO_3$, $MgCO_3$.

The inventive composition may comprise a filler or a filler matrix. The filler matrix can be comprised of one filler or a mixture of different fillers.

The nature of filler of the inventive composition is not particularly limited provided the filler is non-acid reactive.

The size of the filler particles should be such that a homogeneous mixture with the hardenable component(s) forming the resin matrix can be obtained.

Useful fillers include fumed silica, fillers based on non-acid reactive fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including molecular sieves.

The silica is usually dispersed within the resin matrix. The silica particles used in the dental compositions preferably have an average diameter of less than about 200 nm or less than about 100 nm in average diameter. These measurements are preferably based on a TEM (transmission electron microscopy) method, whereby a population is analyzed to obtain an average particle diameter.

A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The average surface area of the silica particles is preferably greater than about 15 $m^2$/g more preferably greater than about 30 $m^2$/g.

Once dispersed in the resin, the silica particles are in a discrete (individual) and unassociated (i.e. non-agglomerated, non-aggregated) condition. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The silica particles which can be used in the dental materials of the invention are preferably substantially spherical and substantially non-porous. Although the silica is preferably essentially pure, it may contain small amounts of stabilizing ion such as ammonium and alkaline metal ions.

Suitable fumed silicas include for example, products sold under the tradename AEROSIL series OX-50, -130, -150, and -200 available from Degussa AG, (Hanau, Germany), and CAB-O-SIL M5 available from Cabot Corp (Tuscola, Ill.).

Optionally, a heavy metal oxide or fluoride can be included in the dental materials of the invention to provide a radiopaque dental material. It is preferred that the heavy metal oxide or fluoride be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. Yttriumtrifluoride and Ytterbiumtrifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, cerium oxide, and combinations thereof. The heavy metal oxide particles may be aggregated. If so, it is preferred that the aggregated particles are less than about 200 nm, and more preferably are less than about 90 nm in average diameter.

Other suitable fillers to increase radiopacity are salts of barium and strontium especially strontium sulphate and barium sulphate.

In another embodiment the filler matrix comprises a nano-sized filler including nano-sized silica.

Preferred nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Tex. (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T4OAS); Akzo Nobel Chemicals GmbH, Leverkusen, Germany (for example, those available under the product designation LEVASIL, e.g., 50/50%, 100/45%, 200/30%, 200 A/30%, 200/40%, 200 A/40%, 300/30% and 500/15%), and Bayer MaterialScience AG, Leverkusen, Germany (for example, those available under the product designation DISPERCOLL S, e.g., 5005, 4510, 4020 and 3030).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles as well as other suitable non acid-reactive fillers according to the present invention can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental composition of the invention.

Besides an inorganic material the filler(s) can also be based on an organic material. Examples of suitable organic filler particles include filled or unfilled pulverized polycarbonates, poly(meth)acrylates, polyepoxides, and the like.

The amount of filler to be used in the filler matrix usually depends on the purpose for which the composition should be used.

Useful amounts for filler(s) include:
at least about 0 wt.-% or at least about 5 wt.-% or at least about 10 wt.-% and/or
up to about 90 wt.-% or up to about 80 wt.-% or up to about 70 wt.-%.

Typical ranges include from about 0 wt.-% to about 90 wt.-% or from about from about 5 wt.-% to about 80 wt.-% or from about 10 wt.-% to about 70 wt.-%.

The inventive composition may also comprise one or more additives as component (G) or part of component (G).

Additives of adjuvants which can be used include accelerators, inhibitors or retarders, absorbers, stabilizers, pigments, dyes, surface tension depressants and wetting aids, antioxidants, and other ingredients well known to those skilled in the art.

The amounts and types of each ingredient in the composition should be adjusted to provide the desired physical and handling properties before and after polymerization.

Examples of dyes or pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual colouring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The colour of the compositions of the invention may be additionally imparted by a sensitizing compound.

Examples of fluoride release agents which can be present include naturally occurring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive moiety so that they will be copolymerized with the resin.

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence and fluoride releasing materials.

In order to increase the flexibility of the dental material, it is also possible to add soluble organic polymers including polyvinyl acetate, and copolymers thereof.

There is no absolute need for these adjuvants or additives to be present, so adjuvants or additives might not be present at all. However, if they are present they are typically present in an amount which is not detrimental to the intended purpose.

Useful amounts for additives include:
at least about 0 wt.-% or at least about 0.5 wt.-% or at least about 1 wt.-% and/or
up to about 15 wt.-% or up to about 10 wt.-% or up to about 5 wt.-%.

Typical ranges include from about 0 wt.-% to about 15 wt.-% or from about from about 0.5 wt.-% to about 10 wt.-% or from about 1 wt.-% to about 5 wt.-%.

The curable composition of the invention can be obtained by combining (including mixing and kneading) the individual components of the composition, preferably under "safe light" conditions.

Suitable inert solvents may be employed if desired when providing the mixture. Any solvent may be used which does not react appreciably with the components of the inventive compositions.

Examples of solvents include, but are not limited to linear, branched or cyclic, saturated or unsaturated alcohols, ketones, esters or mixtures of two or more of said type of solvents with 2 to 10 C atoms. Preferred alcoholic solvents include methanol, ethanol, iso-propanol and n-propanol.

Other suitable organic solvents are THF, acetone, methylethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

The compositions of the invention are particularly well adapted for use as a wide variety of dental materials, which may be filled or unfilled.

Such dental materials include direct aesthetic restorative materials (e.g., anterior and posterior restoratives), adhesives and primers for oral hard tissues, sealants, cavity liners, orthodontic bracket adhesives for use with any type of bracket (such as metal, plastic and ceramic), crown and bridge cements, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

If desired, the tooth can optionally be pre-treated with a primer such as a dentin or enamel adhesive by methods known to those skilled in the art.

Possible uses of the inventive composition in the dental field include the use as anterior or posterior filling, adhesive, cavity liner, flowable, cement, coating composition, root canal filler, root canal sealant or core build-up material.

A typical application process for the inventive composition typically includes the following steps in the desired order:
providing the composition,
placing the composition in contact with a tooth surface (e.g. dentin or enamel),
applying radiation (e.g. visible light) to the composition for a period of time sufficient to initiate the polymerisation process (e.g. about 5 to about 20 s).

Depending on the packaging, the composition is either dispensed from a compule (typically used for single applications) or from a vessel or screw tube (typically used for multiple applications).

As the composition is self-adhesive, no prior etching step or use of a bonding/primer is needed.

The inventive composition is typically stored in a container until use.

If the container has more than one compartment, the composition described in the present text is stored in only one compartment of the container. The composition is not separated into different parts and stored in different compartments of the container.

A one-component system can be stored in a container having only one chamber such as a compule or a screw tube or a syringe. The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. No. 5,893,714 and U.S. Pat. No. 5,865,803, the content of which with regard to the description of compules or containers is herewith incorporated by reference.

The volume of the container is typically in the range from about 0.1 to about 100 ml or from about 0.5 to about 50 ml or from about 1 to about 30 ml.

According to a further embodiment, the inventive composition does typically not contain acid-reactive, basic fillers like the oxides, carbonates and hydroxides of calcium, magnesium, strontium, zinc, acid-reactive fluoroaluminosilicate glasses or mixtures thereof, especially fillers which are able to react with the acidic components of the inventive composition in an ion exchange, neutralization, salt-forming and/or chelate-forming reaction.

Those kinds of fillers can, however, be present in neutralized form, that is, in a form where the filler(s) has(have) already reacted with the acidic component(s) of the composition and thus do(es) not jeopardize the etching and/or self-adhesive properties of the inventive composition.

The pH value of the final composition should, however, still be in a range from about 0 to 5 or 1 to 4.

Further acid-reactive fillers, which are typically not included are those described e.g. in, GB 1,316,129 and WO 95/22956 (Wang et al.).

The presence of a basic filler might negatively affect the adhesion properties due to a neutralization reaction with the monomers comprising an acidic moiety. As known to the skilled person, monomers comprising acidic moieties are typically required to etch the surface of the tooth to be treated and to make a composition self-adhering to dental surfaces.

According to another embodiment, the inventive composition does typically (also) not contain components comprising a sulfinate moiety (especially sulfinate salts such as sodium toluene sulfinate), barbituric acid moiety, thiobarbituric acid moiety, an aryl borate moiety or mixtures thereof.

Thus, according to a further embodiment the inventive composition may not comprise either of the following combinations of components:
  basic filler and component comprising a barbituric or thiobarbituric acid moiety,
  basic filler and component comprising an aryl borate moiety,
  basic filler and component comprising a sulfinate moiety,
  basic filler, component comprising an aryl borate moiety and component comprising a sulfinate moiety.

Unavoidable traces of these components might be present (e.g. due to impurities in the raw materials used). However, those components are typically not willfully added in an amount to participate in the curing reaction.

EXAMPLES

Unless otherwise indicated, all parts and percentages are on a weight basis, all water is de-ionized water, and all molecular weights are weight average molecular weight. Moreover, unless otherwise indicated all Experiments were conducted at ambient conditions (23° C.; 1013 mbar). Moreover, nearly all process steps are conducted under an atmosphere of dry air:

ABBREVIATIONS

Jonol: stabilizer (2,6-ditert.butyl-4-methylphenol)
EDMAB: Ethyl 4-dimethylaminobenzoate
UDMA: 7,7,9-(resp. 7,9,9-)Trimethyl-4,13-dioxo-3,14-dioxa-5,12-diaza-hexadecane-1,16-dioxy dimethacrylate (mixture of isomers)
MPDADM: Methoxypropyl-diethanolamine dimethacrylate
DDDMA: Dodecandioldimethacrylate
TEGDMA: Triethylenglycol dimethacrylate
GDMP: Glycerol dimethacrylate phosphate
MDP: Methacryloyldecylphosphate
PBDM: Propoxylated Bisphenol A dimethacrylate
OX50: Fumed silica
HDK H-2000: Fumed silica
SABS I: Strontiumaluminoborosilicate glass filler, 3% silane treated
SABS II: Strontiumaluminoborosilicate glass filler, 4.6% silane treated
Na-Persulphate: Na-peroxodisulphate/strontiumaluminoborosilicate glass filler (Mixture 50/50)

Measurements

Flexural Strength and E-Modul

This measurement was conducted according to ISO 4049: 2000

Wire Loop Adhesion

This measurement was conducted as follows:

As substrates, bovine teeth were embedded in cold cure epoxy resin and ground to expose dentin or enamel with a 600 grit SiC paper. Finally the surface of each tooth was rinsed with water and gently air-dried. The testing material was filled into the testing mould (diameter: 5 mm) directly fixed on the tooth surface and light cured for 20 s. Bonded specimens (n=5) were tested after 24 hrs storage in de-ionized water at 36° C. in a universal testing machine (Zwick 010) with a crosshead speed of 2 mm/min. To shear off the test buttons a looped orthodontic wire was used.

Example 1 and Comparative Examples 1-3

Formulations including propoxylated Bisphenol A dimethacrylate and GDMP with and without copper salt and persulphate (Table 1)

TABLE 1

| Component | Example 1 wt.-% | C. E. 1 wt.-% | C. E. 2 wt.-% | C. E. 3 wt.-% |
|---|---|---|---|---|
| Jonol | 0.04 | 0.04 | 0.04 | 0.04 |
| Camphorquinone | 0.40 | 0.40 | 0.40 | 0.40 |
| EDMAB | 0.10 | 0.10 | 0.10 | 0.10 |
| PBDM | 12.28 | 12.28 | 12.28 | 12.28 |
| MPDADM | 0.50 | 0.50 | 0.50 | 0.50 |
| DDDMA | 2.38 | 2.38 | 2.38 | 2.38 |
| TEGDMA | 4.17 | 4.17 | 4.17 | 4.17 |
| GDMP | 17.67 | 17.67 | 17.70 | 17.70 |
| Cu (II)-acetate monohydrat | 0.03 | 0.03 | 0.00 | 0.00 |
| OX 50 | 0.10 | 0.10 | 0.10 | 0.10 |
| HDK H-2000 | 4.40 | 4.40 | 4.40 | 4.40 |
| SABS I | 31.78 | 31.78 | 31.78 | 31.78 |
| SABS II | 24.15 | 26.15 | 26.15 | 24.15 |
| Na-Persulphate | 2.00 | 0.00 | 0.00 | 2.00 |

Example 2 and Comparative Examples 4-5

Formulations including urethane(meth)acrylate and GDMP with and without copper salt and persulphate compound (Table 2).

TABLE 2

| Component | Example 2 wt.-% | C. E. 4 wt.-% | C. E. 5 wt.-% |
|---|---|---|---|
| Jonol | 0.04 | 0.04 | 0.04 |
| Camphorquinone | 0.10 | 0.10 | 0.10 |
| EDMAB | 0.40 | 0.40 | 0.40 |
| UDMA | 12.28 | 12.28 | 12.28 |
| MPDADM | 0.50 | 0.50 | 0.50 |
| DDDMA | 2.38 | 2.38 | 2.38 |
| TEGDMA | 4.17 | 4.17 | 4.17 |
| GDMP | 17.67 | 17.67 | 17.70 |
| Cu (II)-acetate monohydrat | 0.03 | 0.03 | 0.00 |
| OX 50 | 0.10 | 0.10 | 0.10 |
| HDK H-2000 | 4.40 | 4.40 | 4.40 |

TABLE 2-continued

| Component | Example 2 wt.-% | C. E. 4 wt.-% | C. E. 5 wt.-% |
|---|---|---|---|
| SABS I | 31.78 | 31.78 | 31.78 |
| SABS II | 24.15 | 26.15 | 26.15 |
| Na-Persulphate | 2.00 | 0.00 | 0.00 |

Overview of adhesion and mechanical properties of formulations including propoxylated Bisphenol A dimethacrylate and GDMP, with and without copper salt and persulphate compound and commercially available product Vertise™ Flow (Kerr)—Table 3

TABLE 3

| | Example 1 | C. E. 1 | C. E. 2 | C. E. 3 | Vertise™ Flow |
|---|---|---|---|---|---|
| Flexural strength [MPa] | 108 ± 9 | 125 ± 14 | 137 ± 6 | 117 ± 5 | 111 ± 6 |
| E-Modulus [MPa] | 5302 ± 119 | 5361 ± 137 | 5515 ± 172 | 5731 ± 195 | 4958 ± 116 |
| Wire loop adhesion, dentin [MPa] | 9.2 ± 2.1 | 1.4 ± 1.9 | 0.7 ± 1.7 | 2.8 ± 3.8 | 0.6 ± 1.6 |

Overview of mechanical and adhesion properties of formulations including urethane(meth)acrylate and GDMP, with and without copper salt and persulphate compound—Table 4.

TABLE 4

| | Example 2 | C. E. 4 | C. E. 5 |
|---|---|---|---|
| Flexural strength [MPa] | 126 ± 8 | 138 ± 5 | 138 ± 9 |
| E-Modulus [MPa] | 5996 ± 116 | 5665 ± 71 | 5694 ± 163 |
| Wire loop adhesion, dentin [MPa] | 9.4 ± 2.9 | 3.9 ± 2.8 | 1.2 ± 1.7 |

The results in Tables 3 and 4 demonstrate that formulations according to the invention with a persulphate and a copper compound (Example 1 and 2) result in good mechanical and adhesion performance, especially with respect to dentin surfaces. Omitting persulphate (Comparative Example 1 and 4) or copper (Comparative Example 3) or both components (Comparative Example 2 and 5) results in a significantly lower adhesion to dentin. The commercially available product Vertise™ Flow (Kerr) also revealed significantly lower adhesion to dentin.

Example 3 and Reference Example 6

Formulations including propoxylated Bisphenol A dimethacrylate and GDMP with and without HEMA (Table 5)

TABLE 5

| Component | Example 3 wt.-% | R. E. 6 wt.-% |
|---|---|---|
| Jonol | 0.04 | 0.04 |
| Camphorquinone | 0.40 | 0.40 |
| EDMAB | 0.10 | 0.10 |
| PBDM | 12.28 | 12.28 |
| MPDADM | 0.50 | 0.50 |
| DDDMA | 0.00 | 2.38 |
| HEMA | 2.38 | 0.00 |
| TEGDMA | 4.17 | 4.17 |
| GDMP | 17.67 | 17.67 |
| Cu (II)-acetate monohydrat | 0.03 | 0.03 |
| OX 50 | 0.10 | 0.10 |
| HDK H-2000 | 4.40 | 4.40 |
| SABS I | 31.78 | 31.78 |
| SABS II | 24.15 | 24.15 |
| Na-Persulphate | 2.00 | 2.00 |

Example 4 and Reference Example 7

Formulations including urethane(meth)acrylate and GDMP with and without HEMA (Table 6).

TABLE 6

| Component | Example 4 wt.-% | R. E. 7 wt.-% |
|---|---|---|
| Jonol | 0.04 | 0.04 |
| Camphorquinone | 0.10 | 0.10 |
| EDMAB | 0.40 | 0.40 |
| UDMA | 12.28 | 12.28 |
| MPDADM | 0.50 | 0.50 |
| DDDMA | 0.00 | 2.38 |
| HEMA | 2.38 | 0.00 |
| TEGDMA | 4.17 | 4.17 |
| GDMP | 17.67 | 17.67 |
| Cu (II)-acetate monohydrat | 0.03 | 0.03 |
| OX 50 | 0.10 | 0.10 |
| HDK H-2000 | 4.40 | 4.40 |
| SABS I | 31.78 | 31.78 |
| SABS II | 24.15 | 24.15 |
| Na-Persulphate | 2.00 | 2.00 |

Example 5 and Reference Example 8

Formulations including propoxylated Bisphenol A dimethacrylate and MDP, with and without HEMA (Table 7)

TABLE 7

| Component | Example 5 wt.-% | R. E. 8 wt.-% |
|---|---|---|
| Jonol | 0.04 | 0.04 |
| Camphorquinone | 0.40 | 0.40 |
| EDMAB | 0.10 | 0.10 |
| PBDM | 12.28 | 12.28 |
| MPDADM | 0.50 | 0.50 |
| DDDMA | 0.00 | 2.38 |
| HEMA | 2.38 | 0.00 |
| TEGDMA | 4.17 | 4.17 |
| MDP | 17.67 | 17.67 |

TABLE 7-continued

| Component | Example 5 wt.-% | R. E. 8 wt.-% |
|---|---|---|
| Cu (II)-acetate monohydrat | 0.03 | 0.03 |
| OX 50 | 0.10 | 0.10 |
| HDK H-2000 | 4.40 | 4.40 |
| SABS I | 31.78 | 31.78 |
| SABS II | 24.15 | 24.15 |
| Na-Persulphate | 2.00 | 2.00 |

Overview of mechanical and adhesion properties of formulations including propoxylated Bisphenol A dimethacrylate and GDMP, with and without HEMA—Table 8.

TABLE 8

| | Example 3 | R. E. 6 |
|---|---|---|
| Flexural strength [MPa] | 111 ± 6 | 108 ± 9 |
| E-Modulus [MPa] | 5740 ± 110 | 5302 ± 119 |
| Wire loop adhesion, dentin [MPa] | 13.9 ± 3.7 | 9.2 ± 2.1 |

Overview of mechanical and adhesion properties of formulations including urethane(meth)acrylate and GDMP, with and without HEMA—Table 9.

TABLE 9

| | Example 4 | R. E. 7 |
|---|---|---|
| Flexural strength [MPa] | 130 ± 6 | 126 ± 8 |
| E-Modulus [MPa] | 6158 ± 198 | 5996 ± 116 |
| Wire loop adhesion, dentin [MPa] | 15.3 ± 3.7 | 9.4 ± 2.9 |

Overview of mechanical and adhesion properties of formulations including propoxylated Bisphenol A dimethacrylate and MDP, with and without HEMA—Table 10.

TABLE 10

| | Example 5 | R. E. 8 |
|---|---|---|
| Flexural strength [MPa] | 108 ± 3 | 104 ± 2 |
| E-Modulus [MPa] | 4581 ± 158 | 4057 ± 86 |
| Wire loop adhesion. dentin [MPa] | 11.3 ± 2.1 | 5.6 ± 1.4 |

The results in Tables 8-10 show that the addition of components such as HEMA (Examples 3, 4 and 5) further increases the adhesion performance of the composition, especially to dentin while maintaining good mechanical properties.

The invention claimed is:

1. A one-component self-adhesive composition for dental use comprising
    a) radically polymerizable component(s) with an acidic moiety as component A,
    b) radically polymerizable component(s) without an acidic moiety as component (B),
    c) an oxidizing agent comprising persulfate(s) as component (C),
    d) transition metal component(s) as component (D),
    e) photoinitiator system as component (E),
    f) optionally non acid-reactive filler(s) as component (F), and
    g) optionally additive(s) as component (G),
    the composition not comprising basic filler(s).

2. The composition according to claim 1, not comprising component(s) comprising a barbituric acid moiety, a thiobarbituric acid moiety, a sulfinate moiety, an aryl borate moiety or mixtures thereof.

3. The composition according to claim 1, wherein the oxidizing agent fulfils at least one of the following features:
    not containing carbon-carbon based moieties,
    being water-soluble.

4. The composition according to claim 1, wherein the transition metal component(s) is selected from organic and/or inorganic salts from titanium, vanadium, chromium, manganese, cobalt, nickel, copper, zinc, either in hydrated or in dry form and mixtures thereof.

5. The composition according to claim 1, wherein the transition metal component is a copper component being selected from copper acetate, copper chloride, copper benzoate, copper acetylacetonate, copper naphthenate, copper carboxylates, copper procetonate, copper complexes, either in hydrated or in dry form and mixtures thereof.

6. The composition according to claim 1, wherein the photoinitiator system is selected from
    a) di-component system(s) comprising an amine and an alpha-diketon component,
    b) three-component system(s) comprising an iodonium salt, a sensitizer and a donor component,
    c) system(s) comprising an acyl or bisacylphosphine oxide.

7. The composition according to claim 1, wherein the radically polymerizable component with an acidic moiety is selected from components with the formula $$A_n\text{-B}—C_m \qquad (I)$$

with A being an ethylenically unsaturated group,
B being a spacer group, selected from (i) linear or branched C1 to C12 alkyl, optionally substituted with other functional groups (ii) C6 to C12 aryl, optionally substituted with other functional groups and (iii) organic group having 4 to 20 carbon atoms bonded to one another by one or more ether, thioether, ester, thioester, thiocarbonyl, amide, urethane, carbonyl and/or sulfonyl linkages, wherein the other functional groups are selected from halogenides and/or OH and
C being an acidic group, with m, n=1, 2, 3, 4, 5 or 6,
    wherein the acidic group comprises one or more carboxylic acid residues, phosphoric acid residues, phosphonic acid residues, sulfinic acid residues, sulphonic acid residues, and mixtures thereof.

8. The composition according to claim 1, wherein the radically polymerizable component without an acidic moiety is selected from mono-, di- or poly-acrylates and methacrylates, bis-acrylates and bis-methacrylates of polyethylene glycols of molecular weight 200-500 g/mol, co-polymerizable mixtures of acrylated monomers, acrylated oligomers, vinyl moieties bearing compounds and mixtures thereof, wherein the radically polymerizable component may be substituted with a hydroxyl group, 1,3-diketo group or both.

9. The composition according to claim 1, wherein component (B) comprises a component (B1) with a hydroxyl group and/or 1,3-diketo group and a component (B2) not having either of these functionalities.

10. The composition according to claim 1 being characterized by at least one of the following features after hardening:
    Flexural strength determined according to ISO 4049:2000: at least 50 MPa,
    E-Modulus determined according to ISO 4049:2000: at least 3500 MPa,
    Adhesion to dentin determined according to wire loop test method: at least 5 MPa,
    Adhesion to enamel determined according to wire loop test method: at least 7 MPa.

11. The composition according to claim 1 comprising the components in the following amounts:
- d) radically polymerizable component(s) with an acidic moiety: from about 3 to about 80 wt.-%,
- e) radically polymerizable component(s) without an acidic moiety: from about 5 to about 65 wt.-%,
- f) oxidizing agent: from about 0.1 to about 10 wt.-%,
- g) transition metal component: from about 0.0001 to about 3 wt.-%,
- h) photoinitiator system: from about 0.1 to about 5 wt.-%,
- i) filler(s): from 0 to about 90 wt.-%,
- j) additives: from 0 to about 15 wt.-%, wt.-% with respect to the weight of the whole composition.

12. The composition according to claim 1 for use as anterior or posterior filling, adhesive, cavity liner, flowable, cement, coating composition, root canal filler, root canal sealant, core build-up material or a combination thereof.

13. The composition according to claim 1 being contained in a container.

14. The composition according to claim 1 being a self-adhesive, photo-curable system.

15. Method comprising the steps of a) applying the composition as described in claim 1 to a surface, b) curing the composition by applying radiation, the method not comprising an additional mixing step and/or etching step.

16. The composition according to claim 7, wherein A comprises a (meth)acryl moiety.

17. The composition according to claim 7, wherein the acidic group comprises one or more of —COOH, —CO—O—CO—, —O—P(O)(OH)OH, —C—P(O)(OH)OH, —SO$_2$H, —SO$_3$H, and mixtures thereof.

* * * * *

UNITED STATES PATENT AND TRADEMARK OFFICE
CERTIFICATE OF CORRECTION

PATENT NO. : 9,132,069 B2
APPLICATION NO. : 14/360373
DATED : September 15, 2015
INVENTOR(S) : Hecht et al.

It is certified that error appears in the above-identified patent and that said Letters Patent is hereby corrected as shown below:

In the Specification

Column 2
Line 14, Delete "persulfate(s)" and insert -- persulfate(s), -- therefor.
Line 15, Delete "component(s)" and insert -- component(s), -- therefor.

Column 3
Line 12, Delete "i.a." and insert -- i.e., -- therefor.

Column 7
Line 50-51, Delete "bis[1-(3-acryloxy-2-hydroxy)]p-" and insert -- bis[1-(3-acryloxy-2-hydroxy)]-p- --, therefor.

Column 10
Line 54, Delete "photoinitator" and insert -- photoinitiator --, therefor.

Column 16
Line 50, Delete "(lithopones)," and insert -- (lithophones), --, therefor.
Line 51, Delete "Neazopon" and insert -- Neozapon --, therefor.

Column 19
Line 59, Delete "Dodecandioldimethacrylate" and insert -- Dodecanedioldimethacrylate --, therefor.
Line 60, Delete "Triethylenglycol" and insert -- Triethyleneglycol --, therefor.

Column 20
Line 27, Delete "(Table 1)" and insert -- (Table 1). --, therefor.

Column 21
Line 13, Delete "Table 3" and insert -- Table 3. --, therefor.

Signed and Sealed this
Fifteenth Day of March, 2016

Michelle K. Lee
*Director of the United States Patent and Trademark Office*

Line 53-54, Delete "(Table 5)" and insert -- (Table 5). --, therefor.

Column 22
Line 54, Delete "(Table 7)" and insert -- (Table 7). --, therefor.

Column 23
Line 43, Delete "adhesion." and insert -- adhesion, --, therefor.